United States Patent [19]

Shoesmith, deceased

[11] Patent Number: Plant 6,401

[45] Date of Patent: Nov. 15, 1988

[54] CHRYSANTHEMUM PLANT NAMED CORNHUSKER

[75] Inventor: Leonard H. Shoesmith, deceased, late of Westfield, England, by May Victoria Shoesmith, executrix

[73] Assignee: Ball Pan Am Plant Co., Parrish, Fla.

[21] Appl. No.: 5,852

[22] Filed: Jan. 21, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Cornhusker characterized by its semi-double flower form and bright yellow ray florets, compact and free branching habit, and by its eight week flowering response.

1 Drawing Sheet

The present invention comprises a new and distinct cultivar of *Chrysanthemum morifolium,* Ramat., hereinafter referred to by the cultivar name Cornhusker.

Cornhusker is a product of a planned breeding program which had the objective of creating new chrysanthemum cultivars having the characteristics of free branching and compact growth habit, early flowering, and very floriferous, producing numerous small semi-double flowers of yellow color. Such traits in combination were not present or needed improvement in previously available commercial cultivars.

Cornhusker was originated from a hybridization made in a controlled breeding program in Westfield-Woking, England by Leonard H. Shoesmith in 1980. The male and female parents are unknown at this time. Cornhusker was discovered and selected as one flowering plant within the progeny of the stated parentage by Leonard H. Shoesmith in November 1981 in a controlled environment in Parrish, Fla.

The first act of asexual reproduction of Cornhusker was accomplished when vegetative cuttings were taken from the initial selection in February 1982 in a controlled environment in Parrish, Fla. by a technician working under formulations established and supervised by Leonard H. Shoesmith. Horticultural examination of selected units initiated in April 1982 has demonstrated that the combination of characteristics as herein disclosed for Cornhusker are firmly fixed and are retained through successive generations of asexual reproduction.

Cornhusker has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Cornhusker, which in combination distinguish this chrysanthemum as a new and distinct cultivar:

1. Compact, freely branching growth habit make Cornhusker suitable for 4" pots or as a garden variety.
2. Eight week flowering response.
3. Semi-double flower form (3 rows of ray florets).
4. Diameter across capitulum 32–40 mm on fully open flowers.

5. Individual ray florets approximately 18 mm long and 6 mm wide.
6. Disc florets yellow when mature, yellow-green when immature.
7. Approximately 68 ray florets per capitulum.
8. Bright yellow ray floret color.
9. Apex of ray florets noticeably indented.

Of the many commercial cultivars known to the present inventor, the most similar in comparison to Cornhusker is Flare. Reference is made to attached Chart A which compares certain characteristics of Cornhusker to those same characteristics of Flare. In comparison to Flare, Cornhusker has a more freely branching habit, faster flowering response, smaller flowers, smaller foliage, and taller flowering height.

The accompanying photographic drawing shows in perspective view typical inflorescence and foliage characteristics of Cornhusker. The photograph is in black and white, with several flowers being shown in color to precisely show true flower color.

In the following description, color references are made to The Royal Horticultural Society Colour Chart. The color values were determined at approximately 2:00 p.m. in September 1986 under fluorescent light at Parrish, Fla.

Classification:

*Botanical.*—*Chrysanthemum morifolium,* Ramat., cv Cornhusker.

*Commercial.*—Garden or pot mum.

INFLORESCENCE

A. Capitulum:
- *Form.*—Flat.
- *Type.*—Semi-double.
- *Diameter across face.*—37 mm.

B. Corolla of ray florets:
- *Color (general tonality from a distance of three meters).*—Bright yellow.
- *Color (upper surface).*—7A.
- *Color (under surface).*—7B.

C. Corolla of disc florets:
- *Color (mature).*—Yellow.
- *Color (immature).*—Yellow-green.

D. Reproductive organs:
- *Androecium.*—Present in disc florets only.
- *Gynoecium.*—Present in both ray and disc florets.

PLANT

A. General appearance:

*Height.*—21 cm when grown in a 4½" pot. Height can differ, depending upon growing conditions and B-Nine applications.

B. Foliage:

*Color (upper surface).*—147A.

*Color (under surface).*—147C.

*Shape.*—Ovate with cleft margins.

CHART A

| | CORNHUSKER VS. FLARE | |
|---|---|---|
| | CORNHUSKER | FLARE |
| FLOWERING RESPONSE | 8 weeks | 9 weeks |
| NUMBER OF | 7 | 5 |

CHART A-continued

| | CORNHUSKER VS. FLARE | |
|---|---|---|
| | CORNHUSKER | FLARE |
| BREAKS | | |
| DIAMETER ACROSS CAPITULUM | Average 37 mm | Average 58 mm |
| MATURE LEAF SIZE - LENGTH × WIDTH | 65 mm × 53 mm | 120 mm × 80 mm |
| FLOWERING PLANT HEIGHT | 21 cm | 17 cm |

The plantlets of Cornhusker and Flare which were used in this comparison were grown together on the same bench in Parrish, Florida, and treated equally in cultural practices.

It is claimed:

1. A new and distinct cultivar of Chrysanthemum plant named Cornhusker, as described and illustrated, and particularly characterized by its semi-double flower form and bright yellow ray florets, compact and free branching habit, and its eight week flowering response.

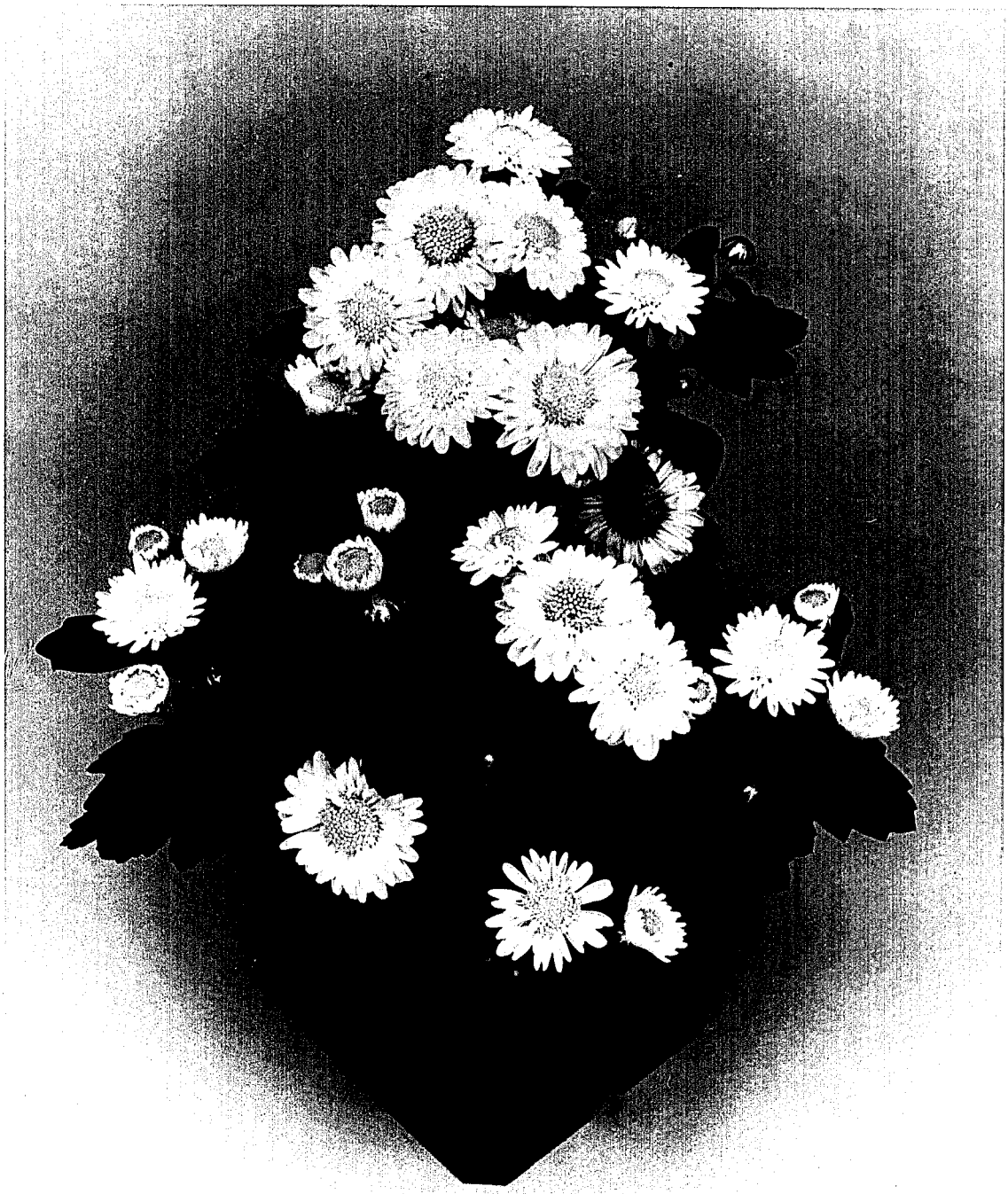

* * * * *